(12) United States Patent
Becco

(10) Patent No.: US 9,700,055 B2
(45) Date of Patent: Jul. 11, 2017

(54) SEED TREATMENT METHOD AND COMPOSITION

(75) Inventor: Carlos Becco, Buenos Aires (AR)

(73) Assignee: Syngenta Participations AG, Basel (CH)

( * ) Notice: Subject to any disclaimer, the term of this patent is extended or adjusted under 35 U.S.C. 154(b) by 515 days.

(21) Appl. No.: 14/114,234

(22) PCT Filed: May 7, 2012

(86) PCT No.: PCT/EP2012/058331
§ 371 (c)(1),
(2), (4) Date: Oct. 28, 2013

(87) PCT Pub. No.: WO2012/152737
PCT Pub. Date: Nov. 15, 2012

(65) Prior Publication Data
US 2014/0051573 A1    Feb. 20, 2014

(30) Foreign Application Priority Data
May 11, 2011  (EP) ..................................... 11165618

(51) Int. Cl.
*A01N 63/00* (2006.01)
*A01N 25/00* (2006.01)
*A01N 37/22* (2006.01)
*A01N 43/36* (2006.01)
*A01N 43/78* (2006.01)
*A01N 43/88* (2006.01)

(52) U.S. Cl.
CPC ............. *A01N 63/00* (2013.01); *A01N 25/00* (2013.01); *A01N 37/22* (2013.01); *A01N 43/36* (2013.01); *A01N 43/78* (2013.01); *A01N 43/88* (2013.01)

(58) Field of Classification Search
None
See application file for complete search history.

(56) References Cited

U.S. PATENT DOCUMENTS

| 5,300,127 A | 4/1994 | Williams | |
|---|---|---|---|
| 8,466,087 B2 * | 6/2013 | Goodwin | A01C 1/06 504/100 |
| 2010/0125040 A1 * | 5/2010 | Weiss | A01N 43/16 504/100 |
| 2010/0144531 A1 * | 6/2010 | Aramaki | A01N 43/40 504/223 |

FOREIGN PATENT DOCUMENTS

| WO | 2005062899 A2 | 7/2005 |
|---|---|---|
| WO | 2007003319 A2 | 1/2007 |

OTHER PUBLICATIONS

International Search Report for International Application No. PCT/EP2012/058331 dated Jul. 25, 2012.

* cited by examiner

*Primary Examiner* — Alton Pryor
(74) *Attorney, Agent, or Firm* — Brian D. McAlhaney

(57) ABSTRACT

A method of treating seeds, comprising: providing a batch of seeds; adding a first mixture comprising at least one insecticide, at least one fungicide, and at least one coating agent to the seeds over a period of about 6 to 15 seconds; homogenizing the seeds for 5 to 25 seconds; adding a second mixture comprising at least one inoculant and at least one protectant to seeds over a period of about 6 to 15 seconds; and homogenizing the seeds for about 5 to 25 seconds.

14 Claims, No Drawings

SEED TREATMENT METHOD AND COMPOSITION

This application is a 371 of International Application No. PCT/EP2012/058331 filed May 7, 2012 which claims priority to European Patent Application No. EP11165618.7 filed May 11, 2011, to which the contents of all are incorporated herein by reference.

FIELD OF THE INVENTION

The present invention relates to methods and compositions for treating plant seeds, seeds treated with a pesticidal composition and uses thereof.

BACKGROUND OF THE INVENTION

Seed treatments are widely used in agriculture. Often they are relied upon to impart pest resistance properties to the seed or resulting plant: application of pesticidal compounds to a seed can reduce damage to the seed during storage, germination, when planted, and also protect the emerging plant from pests. This can help achieve uniform stand establishment which not only has the benefit of protecting an investment in seeds themselves, but also maximises plant performance per unit land.

Some seed treatments have less of a preventative effect and instead enhance performance of the plants or crops. One example is treatment with inoculants of Rhizobiaceae which can increase the nitrogen uptake of legumes. This can result in consistent performance during unfavourable conditions, or improved performance during standard conditions. Methods of increasing plant productivity are also discussed in WO 08/37489.

Some seed treatments incorporate preventative treatments and enhancements. WO 05/62899 describes a combination treatment having a fungicide and/or insecticide in combination with one or more plant inducers and an optional innoculant.

Because of the tangible benefits which can be achieved by treating seeds, formulation methods and materials have developed to provide properties such as improved adherence, reduced dust-off, delayed release, improved plantability and the like. Methods and devices for treating seeds have also evolved and at present a wide range of options are available for preparing commercial quantities of treated seeds.

But despite advances in the field, there remains a need to provide new and innovative seed treatment solutions to achieve optimum plant potential.

SUMMARY OF THE INVENTION

It is therefore an object of the invention to provide a method and composition for seed treatment.

According to a first embodiment of the invention, there is provided a method of treating seeds which comprises providing a batch of seeds, adding a first mixture to the seeds over a period of about 6 to 15 seconds, homogenizing the seeds for about 5 to 25 seconds, adding a second mixture to the seeds over a period of about 6 to 15 seconds, homogenizing the seeds for about 5 to 25 seconds, and optionally drying the seeds.

The first mixture can comprise at least one insecticide, at least one fungicide, and at least one coating agent. An example of an insecticide is thiamethoxam. An example of a fungicide is fludioxonil, metalaxyl-M, or mixtures thereof. Examples of coating agents are Disco AG L203, Disco AG L204, Disco AG L232, Disco AG L800, Flo Rite 1127, PF 12, PF 16, talcum and calcium carbonate or mixtures thereof. The first or second mixture can additionally comprise a nematicide, for example, abamectin or *Pasteuria* spp.

The second mixture can comprise at least one inoculant and at least one protectant. An example of an inoculant is *Bradyrhizobium* spp. An example of a protectant is PRE-MAX.

According to an embodiment of the invention, a method of treating seeds as described above is provided, wherein the seeds are from a legume plant, for example soybean.

According to an embodiment of the invention, a method of increasing yield, enhancing plant growth, and/or increasing seed plantability is provided which comprises treating a seed of the plant with a method as described herein.

According to an embodiment of the invention, a seed treated according to the method described herein is provided.

As used herein, the term "seed" refers to plant propagation or generative material which can be used for multiplication of the plant such as true seeds, partial seeds, grains, suckers, tubers, corms, bulbs, rhizomes, and fruit.

Although it is expected that the present method can be applied to a seed in any physiological state, it is preferred that the seed be in a sufficiently durable state that it incurs no or no significant damage during treatment. The seed would preferably also be biologically stable to the extent that the treatment would cause no or no significant biological damage. It is believed that the treatment can occur any time between harvest and sowing. The seed may also be primed or pre-germinated before or after the treatment.

A first mixture applied to the seeds includes at least one insecticide, at least one fungicide, at least one coating agent, and optionally at least one nematacide.

Examples of insecticide include neonicotinoids, carbamates, diamides, spinosyns, phenylpyrazoles, pyrethroids and sulfoxaflor. For example, thiamethoxam, clothianidin, imidacloprid, acetamiprid, dinotefuran, nitenpyram, thiacloprid, thiodicarb, aldicarb, carbofuran, furadan, fenoxycarb, carbaryl, sevin, ethienocarb, fenobucarb, chlorantraniliprole, cyantraniliprole, flubendiamide, spinosad, spinetoram, lambda-cyhalothrin, gamma-cyhalothrin, tefluthrin, fipronil, pyrometrizine, and mixtures thereof. A preferred insecticide according to the present invention is thiamethoxam.

Examples of fungicides include strobilurin fungicides, azole fungicides, conazole fungicides, triazole fungicides, amide fungicides, benzothiadiazole fungicides. For example azoyxstrobin, paclobutrazol, difenoconazole, isopyrazam, epoxiconazole, acibenzolar, acibenzolar-S-methyl, chlorothalonil, cyprodinil, fludioxonil, mandipropamid, picoxystrobin, propiconazole, pyraclostrobin, tebuconazole, thiabendazole, trifloxystrobin, mancozeb, chlorothalonil, metalaxyl-M (mefenoxam), metalaxyl, ametoctradin, prothioconazole, triadimenol, cyproconazole, sedaxane, cyprodinil, penconazole, boscalid, bixafen, fluopyram, penthiopyrad, fluazinam, fenpropidin, cyflufenamid, tebuconazole, trifloxystrobin, fluxapyroxad, penflufen, fluoxastrobin, kresoxim-methyl, benthiavalicarb, dimethomorph, amisulbrom, cyazofamid, flusulfamide, and mixtures thereof. Preferred fungicides according to the present invention include fludioxonil and metalaxyl-M or mixtures thereof.

Coating agents used for seed treatment include binders, flow agents, pigments, and other ingredients well known in the art. Polymers are often used. Preferred coating agents according to the invention are Disco AG L203, Disco AG L 204, Disco AG L232, and Disco AG L800 (all Incotec, Netherlands); Flo Rite 1127, PF 12, and PF 16 (for example applied at a rate of 2-4 g/kg seed) (all Becker Underwood, USA); talcum (for example applied at a rate of 2-4 g/kg seed); and calcium carbonate (fine grade preferred, for example applied at a rate of about 4 g/kg seed).

Examples of nematicides include avermectin nematicides, carbamate nematicides, and organophosphorous nematicides, for example abamectin, emamectin benzoate, benomyl, carbofuran, carbosulfan, cloethocarb, alanycarb, aldicarb, aldoxycarb, oxamyl, tirpate, diamidafos, fenamiphos, fosthietan, phosphamidon, cadusafos, chlorpyrifos, dichlofenthion, dimethoate, ethoprophos, fensulfothion, fosthiazate, heterophos, isamidofos, isazofos, phorate, phosphocarb, terbufos, thionazin, triazophos, imicyafos, mecarphon, acteoprole, benclothiay, chloropicrin, dazomet, fluensulfone, furfural, metam, methyl iodide. Methyl isothiocyanate, xylenols, and mixtures thereof. Nematicides also include nematicidally active biological organisms such as a bacteria or fungus. For example, *Bacillus firmus, Bacillus cereus, Bacillus* spp, *Pasteuria* spp, *Pochonia chlamydosporia, Pochonia* spp, and *Streptomyces* spp. A preferred nematicide according to an embodiment of the present invention is abamectin.

Where a biological nematicide is employed, it may be preferable to add it with the second mixture or even after the inventive seed treatment has been completed. Chemical nematicides may preferably be added with the first mixture A second mixture applied to the seeds includes at least one inoculant and at least one protectant.

Examples of inoculants which can be used in the present invention include species in the family Rhizobiaceae such as *Rhizobium* spp, *Bradyrhizobium* spp, *Sinorhizobium* spp, *Azorhizobium* spp, *Mesorhizobium* spp, *Allorhizobium* spp, and other agriculturally active inoculants. A preferred inoculant according to an embodiment of the present invention is *Rhizobium*.

Protectants are commonly used in conjunction with inoculants. They generally incorporate nutrients for the bacteria as well as water or other solvent. A common feature is that they also help adhere the bacteria to the surface of the seed and protect the bacteria against desiccation or basic mechanical or chemical damage. Examples include inorganic nutrient salts and polysaccharides. Any suitable protectants could be used in the present invention; a preferred protectant according to an embodiment of the invention is PREMAX (Rizobacter Argentina S.A.).

Compounds referred to herein using a common or trade name are known in the art and thoroughly described in "The Pesticide Manual", Fifteenth Edition, Edited by Clive Tomlin, British Crop Protection Council.

It is contemplated that the invention could be used on a variety of commercial crops. For example, leguminous plants, such as soybean, bean, lentil, pea, alfalfa, peanut, and clover may benefit most particularly from the invention because it provides inoculant which will help the plants fix nitrogen. However, the invention could also be used with grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or black-berries; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

For ease of description, the present invention will be disclosed using soybean embodiments. Examples of suitable varieties include, but are not limited to, SPS 3900, SPS 4670, SPS 4900, SPS 4×4, SPS 5×2, SPS 5×9, SPS 7×0, SPS 3×1, SPS 4×0, SPS 4×99, SPS 5×5, SPS 6×2, and SPS 8×0, all available from SPS Argentina S.A; and DM 2200, DM 3070, DM 3500, DM 3700, DM 3810, DM 4210, DM 4250, DM 4670, DM 4970, DM 5.1i, DM 5.5i, DM 5.8i, DM 5.9i, DM 6.2i, DM 6500, DM 7.0i, DM 7.8i, and DM 8002, all available from DONMARIO Semillas, Argentina, and Monsoy 7578RR.

All types of varieties can be treated according to the present invention. Hybrid and transgenic plants are explicitly encompassed by the present invention. Often a grower will pay a premium for hybrid or transgenic plant seed thus motivating the use of the present invention to help secure their investment with the inventive seed treatment method and composition. At the same time, lower-price seed which may be bred using conventional techniques can be treated according to the invention thus providing improved performance despite the lower investment in seed.

The inventive seed treatment method may be applied using any seed treatment equipment or apparatus. Many existing seed treaters could be used with the present invention, for example Cimbria Centricoaters CC 50, CC 150, and CC 250 (NS Cimbria, Thisted, Denmark).

According to the present invention, "crop enhancement" means an improvement in plant vigour, an improvement in plant quality and/or improved tolerance to stress factors.

According to the present invention, an "improvement in plant vigour" means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an "improvement in plant quality" means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants), improved post-harvest characteristics (e.g. enhanced shelf-life and/or storage stability, easier processability, easier extraction of compounds) and/or improved seed quality (e.g. for use in following seasons). A plant with improved quality may have an increase in any of the aforementioned traits or any combination or two or more of the aforementioned traits.

According to the present invention, an "improved tolerance to stress factors" means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

According to the present invention, an "improved plantability" means that planting of treated seed can be performed more efficiently, including more quickly; more reliably; more predictably; with reduced maintenance or adjustments to planting equipment or other similar benefits. Benefits are primarily experienced in machine-assisted or mechanised planting. When equipment is optimised for precision planting and a reliable and accurate planting of seed at minimal input from the grower (in terms of cost, time and other inputs) it creates benefit for the overall farm economy.

DETAILED DESCRIPTION OF THE INVENTION

It has surprisingly been found that providing a composition including an insecticide, a fungicide, a coating agent, an inoculant, and a protectant to seeds using a unique treatment method can provide seeds which are capable of growing into plants which exhibit enhanced performance. For example, the inventive treatment allows a grower to harvest an increased yield as compared to crops from untreated seeds or seeds treated using conventional methods and compositions.

The batch size which is suitable for the present invention is one which allows good distribution of product onto the seeds. For commercial soybean treaters, a batch size of 50-100 kg may be preferred.

Usage rates for each pesticidal component of the mixtures which are be used in the present invention are those which provide pesticidal activity for the particular plant in the particular geographic region where it will be planted. Standard ranges are well known in the art and are often guided by local regulatory requirements, which may set minimum and maximum levels to be applied to a seed. An example of a suitable range for a particular pesticide product is the range given on the product label. Pesticidal activity should be understood to mean that which will kill or materially inhibit the growth, proliferation, division, reproduction, or spread of a pest.

The amount of coating agent, inoculant, and protectant will likewise depend on various factors, such as the compounds employed; the seed type treated; the proposed planting conditions; and the expected climactic conditions. Using the guidance provided herein a skilled person will be able to determine the specific amounts which would be suitable for a seed treatment according to the invention.

Typically, formulated products (as opposed to pure active ingredient) are used in seed treatments. For convenience of supply and ease of use formulated products are preferred according to the invention.

According to the inventive treatment method, a first mixture is provided which comprises an insecticide, a fungicide, and a coating agent. A chemical nematicide may also be included in the first mixture.

The first mixture is generally applied by spraying or otherwise feeding the mixture or components into the treatment equipment; the spray application time can last from about 6 to 15 seconds, for example, 6 seconds, 7 seconds, 8 seconds, 9 seconds, 10 seconds, 11 seconds, 12 seconds, 13 seconds, 14 seconds, or 15 seconds.

A first homogenization step is then performed. During this step, the machinery continues to move the seeds about in the treatment apparatus but there are no substantial additions or removals of material. This allows seeds which have less of the composition to adsorb or absorb more, those seeds with excess composition may release some. To some extent the treated seeds begin to dry although the seeds may not be dry at the conclusion of the step.

The first homogenization step may last for approximately 5 to 25 seconds. According to a preferred embodiment, the first homogenization step is 10 to 20 seconds, for example, 10 seconds, 11 seconds, 12 seconds, 13 seconds, 14 seconds, 15 seconds, 16 seconds, 17 seconds, 18 seconds, 19 seconds, or 20 seconds.

A second mixture is then provided which comprises an inoculant and a protectant. If the second mixture is to be stored for any significant period before being applied to seeds it may be advisable to stir the mixture. Once prepared, there may be a maximum time before use depending primarily on the inoculant strain(s) and environmental conditions. For example, it may be preferred to use the second mixture within 6 hours or preparing. The second mixture is applied by spraying; the spray application time can last from about 6 to 15 seconds, for example, 6 seconds, 7 seconds, 8 seconds, 9 seconds, 10 seconds, 11 seconds, 12 seconds, 13 seconds, 14 seconds, or 15 seconds.

A second homogenization step is performed. During this step, the machinery continues to move the seeds about in the treatment apparatus but there are no substantial additions or removals of material. To some extent the treated seeds begin to dry although the seeds may not be dry at the conclusion of the step. The second homogenization step may last for approximately 5 to 25 seconds. According to a preferred embodiment, the second homogenization step is 5 to 20 seconds, for example, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, or 20 seconds.

The treated batch is then downloaded and placed in an appropriate receptacle. To dry the seeds they may be stored at room temperature (e.g. 15 to 30° C.) and preferably low or moderate humidity. In facilities where treated seeds are dried outdoors or in open air circulation it may be preferred to dry the seeds during daytime, because nights can often be higher humidity conditions. Drying the seeds at higher humidity levels can cause undesirable clumping of the seeds.

Some equipment may be capable of carrying out the drying step such that the batch need not be downloaded and dried separately but only downloaded once dry and ready for packaging/storage or use.

Where further crop protection agents such as fertilisers or pesticides are to be applied to the same seeds or later to the emerging/growing plants, they may be applied by any known methods, including by adding the desired additional materials into the first or the second mixture or during a further addition step.

The following data are provided by way of example and not limitation.

Formulation Example 1 Formulation A

A 100 kg batch of soybean seeds SPS 3900 (DONMARIO Semillas, Argentina) were placed in a Cimbria Centricoater CC 250 (NS Cimbria, Denmark). Added to the seeds via spray injection was a mixture of thiamethoxam 36 ml ai/100 kg seed (CRUISER 60 FS, Syngenta Agro), fludioxonil 2.5 ml ai/100 kg seed and metalaxyl-M 3.75 ml ai/100 kg seed (Apron Maxx RFC, Syngenta Agro), and coating agent in the form of film coat liquid 0.15 l/100 kg seed (DISCO AG L203, Incotec, Netherlands). The application time was 10 seconds.

The treatment was paused to homogenize for 20 seconds.
Inoculant comprising a mixture of Bradyrhizobium sp 0.4 l/100 kg seed (inoculant contains approximately $1\times10^{10}$ bacteria/ml, RIZO-LIQ LLI, Rizobacter Argentina S.A.) and protectant 0.14 l/100 kg seed (50% water, 50% inorganic nutrient salts and polysaccharides, PREMAX, Rizobacter Argentina S.A.) was added to the seeds by spraying. The application time was 10 seconds.

The treatment was paused to homogenize for 20 seconds.
The treated batch was then removed from the equipment and allowed to dry at 20° C. and 75% humidity for 24 hours.

Formulation Example 2 Formulation B

A 100 kg batch of soybean seeds SPS 3900 (DONMARIO Semillas, Argentina) were placed in a Cimbria Centricoater CC 250 (NS Cimbria, Denmark). Added to the seeds via spray injection was a mixture of thiamethoxam 36 ml ai/100 kg seed (CRUISER 60 FS, Syngenta Agro), fludioxonil 2.5 ml ai/100 kg seed and metalaxyl-M 3.75 ml ai/100 kg seed (Apron Maxx RFC, Syngenta Agro), abamectin 50 ml ai/100 kg seed (AVICTA 50 FS, Syngenta Agro), and coating agent in the form of film coat liquid 0.3 l/100 kg seed (DISCO AG L203, Incotec, Netherlands). The application time was 10 seconds.

The treatment was paused to homogenize for 20 seconds.
Inoculant comprising a mixture of Bradyrhizobium sp 0.4 l/100 kg seed (inoculant contains approximately $1\times10^{10}$ bacteria/ml, RIZO-LIQ LLI, Rizobacter Argentina S.A.) and protectant 0.14 l/100 kg seed (50% water, 50% inorganic nutrient salts and polysaccharides, PREMAX, Rizobacter Argentina S.A.) was added to the seeds by spraying. The application time was 10 seconds.

The treatment was paused to homogenize for 20 seconds.
The treated batch was then removed from the equipment and allowed to dry at 20° C. and 75% humidity for 24 hours.

Biological Example 1 Field Trial

Soybean seeds of varieties DM 4670 and SPS 3900 (both DONMARIO Semillas, Argentina) were treated as described with relation to Formulation B above. Seeds were also treated with variations on Formulation B, using different agrochemical components in mixture 1. An outdoor field trial was prepared with test plots each measuring 50 m×1000 m. Five replicates were used. Each plot was planted with seeds spaced in rows 52 cm apart, at a depth of 2 cm. Control plots were planted in the same manner and maintained the same way, using seeds of the same variety which were given the same inoculant treatment but not the first mixture.

During plant development, fertilizers and irrigation were used equally among the plots according to prevailing conditions, according to standard practice.

At maturity, the soybeans were harvested from each plot using a standard harvester. The harvested plants were processed according to standard procedures and yield was measured and extrapolated to a kilogram per hectare measurement. Yields from the two soybean varieties were averaged. Data are presented below in Table 1.

TABLE 1

Soybean Yields

| Test plot | Treatment Compound | Average Yield (kg/ha) |
|---|---|---|
| 1 (Control) | Bradyrhizobium sp Premax | 4063 |
| 2 | Thiamethoxam Fludioxonil Metalaxyl-M Abamectin L203 | 4389 |

TABLE 1-continued

Soybean Yields

| Test plot | Treatment Compound | Average Yield (kg/ha) |
|---|---|---|
| 3 | Bradyrhizobium sp Premax<br>Fludioxonil<br>Metalaxyl-M<br>L203<br>Bradyrhizobium sp Premax | 4153 |
| 4 | Fludioxonil<br>Metalaxyl-M<br>Abamectin<br>L203<br>Bradyrhizobium sp Premax | 4276 |

As is evident from the data in Table 1, the best result was a yield of 4389 kg/ha achieved with the use of Formulation B (test plot 2). Other agrochemical compositions in mixture 1 still provided improved yield over the control (test plots 3 and 4). The inventive method provided a yield increase of up to 8%.

Plantability Example 1 Test Treatment

A 10 kg batch of soybean seeds Monsoy 7578RR (seed size 6.5 mm) were placed in an Arktos Africa seed treater. Added to the seeds via spray injection was a first mixture of fludioxonil, metalaxyl-M and thiabendazol in the form of 10 ml MAXIM ADVANCED (Syngenta Agro), thiamethoxam in the form of 6 ml CRUISER 60 FS (Syngenta Agro), and coating agent in the form of 5 ml Disco AG L232 and 15 ml Disco AG L800 (both Incotec, Netherlands).

The application time was 10 seconds. The seeds were homogenized for 10 seconds.

A second mixture was added to the seeds by spraying. It comprised 40 ml Bradyrhizobium sp (inoculant contains approximately $1 \times 10^{10}$ bacteria/ml, RIZO-LIQ LLI, Rizobacter Argentina S.A.) and 14 ml protectant (50% water, 50% inorganic nutrient salts and polysaccharides, PREMAX, Rizobacter Argentina S.A.).

The application time was 10 seconds. Then the seeds were homogenized for 5 seconds and discharged.

Control Treatment

In order to evaluate the performance of seeds treated according to the inventive method, identical seeds and agents were applied using a simultaneous application method. That is, a 10 kg batch of Monsoy 7578RR seed was placed in an Arktos Africa treater. A mixture of fludioxonil, metalaxyl-M and thiabendazol in the form of 10 ml MAXIM ADVANCED (Syngenta Agro), thiamethoxam in the form of 6 ml CRUISER 60 FS (Syngenta Agro), coating agent in the form of 5 ml Disco AG L232 and 15 ml Disco AG L800 (both Incotec, Netherlands), 40 ml Bradyrhizobium sp (inoculant contains approximately $1 \times 10^{10}$ bacteria/ml, RIZO-LIQ LLI, Rizobacter Argentina S.A.) and 14 ml protectant (50% water, 50% inorganic nutrient salts and polysaccharides, PREMAX, Rizobacter Argentina S.A.) was sprayed on the seeds.

The application time was 10 seconds. Then the seeds were homogenized for 15 seconds and discharged.

Thirty days after treatment, test and control seeds were placed in a Corn counter V3.2 machine having a planting disk with 90 holes (8.5 mm) in a double line. A 3 mm flat ring was used to couple the disc together, and the scrapper trigger positioned downward. Four thousand seeds from each group were evaluated.

| | Multiple seeds in single target (%) | Correct planting distance (%) | Missed target (%) | Multiple missed target (%) | Planting rate (%) |
|---|---|---|---|---|---|
| Test Treatment | 21.69 | 60.50 | 16.47 | 1.34 | 97.68 |
| Control Treatment | 22.42 | 56.86 | 18.92 | 1.81 | 96.65 |

The correct planting distance was found where the planting distance between seeds was +/−25% of the target distance. The expected targets where a single seed should have been planted were evaluated: where a single seed was missing, it was counted as a missed target (calculated as a percentage of the total number of targets) and where two or more consecutive targets were missed, they were counted as a multiple missed target.

As seen from the data, seeds treated according to the inventive method showed better plantability. An increased planting rate and lower incidence of duplicate seeds in a single target or completely missed targets will allow for a more even stand of plants, which contributes to better growing conditions and ultimately increased yield per unit area planted.

Plantability Example 2

Using the methods described in Plantability Example 1, a different treatment mixture was evaluated. For the test seeds the first mixture contained fludioxonil and metalaxyl-M in the form of 10 ml APRON MAXX (Syngenta Agro), thiamethoxam in the form of 6 ml CRUISER 60 FS (Syngenta Agro), and coating agent in the form of 5 ml Disco AG L204 and 15 ml Disco AG L800 (both Incotec, Netherlands).

The second mixture was 40 ml Bradyrhizobium sp (inoculant contains approximately $1 \times 10^{10}$ bacteria/ml, RIZO-LIQ LLI, Rizobacter Argentina S.A.) and 14 ml protectant (50% water, 50% inorganic nutrient salts and polysaccharides, PREMAX, Rizobacter Argentina S.A.).

For the control, the same components and amounts of the first and second mixture were applied in a single step as described above.

Results were as follows:

| | Multiple seeds in single target (%) | Correct planting distance (%) | Missed targets target (%) | Multiple missed (%) | Planting rate (%) |
|---|---|---|---|---|---|
| Test Treatment | 23.11 | 54.14 | 20.84 | 1.91 | 95.88 |
| Control Treatment | 25.40 | 50.43 | 20.04 | 4.13 | 88.38 |

Again the data show an improved plantability for seeds treated according to the invention.

The invention claimed is:
1. A method of treating seeds, comprising:
   providing a batch of seeds;
   a) adding a first mixture comprising at least one neonictinoid insecticide, at least one fungicide selected from the group consisting of azole fungicides, conazole fungicides, triazole fungicides, benzothiadiazole fungicides, fludioxonil and mixtures thereof, another fungicide selected from the group consisting of metalaxyl-M, metalaxyl, cyprodinil, boscalid, bixafen, penflufen, fluxapyroxad, flusulfamide, and mixtures thereof, and at least one coating agent to the seeds over a period of about 6 to 15 seconds;

b) homogenizing the seeds for 5 to 25 seconds;

c) adding a second mixture following said (a) and (b) comprising at least one inoculant comprising a species in the family Rhizobiaceae and at least one protectant to the seeds over a period of about 6 to 15 seconds; and d) homogenizing the seeds for about 5 to 25 seconds after step (c).

2. A method according to claim 1, further comprising drying the seeds after the homogenizing (d).

3. A method according to claim 1, wherein the homogenizing (b) is 10 to 20 seconds and/or the homogenizing (d) is 5 to 20 seconds.

4. A method according to claim 1, wherein the insecticide is thiamethoxam.

5. A method according to claim 1, wherein the fungicide is fludioxonil, metalaxyl-M, or mixtures thereof.

6. A method according to claim 1 wherein the inoculant is *Bradyrhizobium* spp.

7. A method according to claim 1, wherein the protectant comprises at least one inorganic nutrient salt and at least one polysaccharide.

8. A method according to claim 1, wherein the first mixture and/or the second mixture further comprises a nematicide.

9. A method according to claim 1, wherein the plant is a legume.

10. A method according to claim 9, wherein the legume is soybean.

11. A method of increasing plant yield, comprising treating a seed of the plant with the method according to claim 1.

12. A method of enhancing plant growth, comprising treating a seed of a plant with the method according to claim 1.

13. A method of enhancing seed plantability, comprising treating seed with the method according to claim 1, and planting the seed.

14. A seed treated with the method according to claim 1.

* * * * *